United States Patent [19]

Furst et al.

[11] 4,193,921

[45] Mar. 18, 1980

[54] PREGNANE DERIVATIVES

[75] Inventors: Andor Fürst, Basel; Ludwig Labler, Allschwil; Werner Meier, Bottmingen, all of Switzerland

[73] Assignee: Hoffmann-La Roche Inc., Nutley, N.J.

[21] Appl. No.: 841,430

[22] Filed: Oct. 12, 1977

[30] Foreign Application Priority Data

Oct. 14, 1976 [CH] Switzerland ............ 13006/76
Sep. 8, 1977 [CH] Switzerland ............ 11011/77

[51] Int. Cl.$^2$ .............................................. C07J 71/00
[52] U.S. Cl. ........................ 260/239.55 R; 260/397.1; 260/397.47; 260/397.5; 206/397.2
[58] Field of Search ............ 260/239.55, 397.1, 397.2, 260/397.5

[56] References Cited

U.S. PATENT DOCUMENTS

| | | | |
|---|---|---|---|
| 3,901,928 | 8/1975 | Hesse et al. | 260/397.2 |
| 3,907,843 | 9/1975 | De Luca et al. | 260/397.2 |
| 3,966,777 | 6/1976 | Mazur et al. | 260/397.2 |
| 4,022,768 | 5/1977 | Matsunaga et al. | 260/397.1 |
| 4,022,891 | 5/1977 | Takeshita et al. | 260/239.55 R |
| 4,046,760 | 9/1977 | Jones et al. | 260/397.2 |
| 4,088,760 | 5/1978 | Benson et al. | 260/397.2 |

FOREIGN PATENT DOCUMENTS 2400189 7/1975 Fed. Rep. of Germany ........ 260/397.2

OTHER PUBLICATIONS

Barton et al., J.C.S. Chem. Comm. (1974), p. 203.
Barton et al., J. Am. Chem. Soc. 95 (1973), p. 2748.
Steroid Reactions by Dyerossi (1963), pp. 227 and 228.
Mitra et al., "Journal of Organic Chem." 39 (1974), p. 2931.
Lam et al., "Steroids" 26 (1975), p. 422.
Freeman et al. "Tetrahedron Letters" (1975) 261.

*Primary Examiner*—Elbert L. Roberts
*Attorney, Agent, or Firm*—Jon S. Saxe; George M. Gould; James H. Callwood

[57] ABSTRACT

The present invention relates to pregnane derivatives of the formula

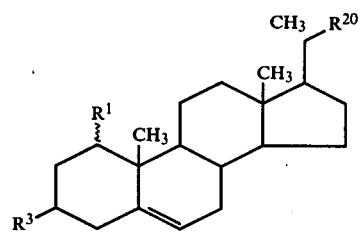

wherein $R^1$ and $R^3$ are hydroxyl groups or readily cleavable etherified or esterified hydroxyl groups and $R^{20}$ is hydroxymethyl or readily cleavable etherified or esterified hydroxy methyl, formyl, carboxyl or carbalkoxy useful as intermediates for the preparation of 1α-hydroxycholecalciferols. The present invention also relates to processes for the preparation of the pregnane derivatives and the intermediates thereof.

12 Claims, No Drawings

PREGNANE DERIVATIVES

DESCRIPTION OF THE INVENTION

The present invention relates to novel pregnane derivatives and to a method for their preparation. In one aspect the present invention relates to novel pregnane derivatives of the formula

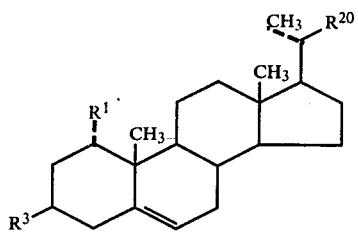

wherein $R^1$ and $R^3$ are hydroxyl groups or readily cleavable etherified or esterified hydroxyl groups and $R^{20}$ is hydroxymethyl or readily cleavable etherified or esterified hydroxymethyl, formyl, carboxyl or carbalkoxy.

Ether groups $R^1$ or $R^3$, which can be readily cleaved, i.e., without modification at other positions of the molecule, are, by way of example, groups of the formula $R^X O$—$C(R^J, R^Z)$—O—, wherein $R^J$ is hydrogen or alkyl of 1 to 6 carbon atoms, $R^X$ and $R^Z$ are alkyl of 1 to 6 carbon atoms or $R^X$ and $R^Z$ together are alkylene of 3 to 6 carbon atoms. Examples of such groups are tetrahydropyran-2-yloxy and methoxymethoxy. Examples of esterified hydroxyl groups $R^1$ and $R^3$ are formyloxy and alkanoyloxy of 2 to 4 carbon atoms, such as acetoxy. Examples of readily cleavable hydroxymethyl groups denoted by $R^{20}$ are the formyloxymethyl group and $C_{2-4}$-alkanoyloxymethyl groups such as the acetoxymethyl group, as well as the bromomethyl group and the p-toluenesulphonyloxymethyl group. Examples of carbalkoxy groups $R^{20}$ are carbomethoxy and carboethoxy.

In the formulas presented herein, the various substituents are illustrated as joined to the steroid nucleus by one of these nations: a solid line (—) indicating a substituent which is in the β-orientation (i.e., above the plane of the molecule), a dotted line (- - - -) indicating a substituent which is in the α-orientation (i.e., below the plane of the molecule) or a wavy line (~) indicating a substituent which may be in the α- or β-orientation. The formulas have all been drawn to show the compounds in their absolute sterochemical configurations. Since the starting materials are derived from naturally occurring stigmasterol, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively. Optically active products can then be prepared by resolution of the racemic products utilizing in the preparation thereof standard resolution techniques well known in the steroid art.

The nomenclature adopted to define absolute configuration of substituents bound to carbon atom 20 of the steroid nucleus is described in the Journal of Organic Chemistry, 35, 2849 (1970) under the title "IUPAC Tentative Rules for the Nomenclature of Organic Chemistry. Section E. Fundamental Stereochemistry".

The compounds of formula I are prepared according to the invention by epoxidizing a compound of formula

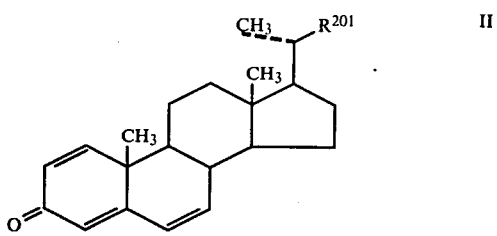

wherein $R^{201}$ is hydroxymethyl or readily cleavable etherified hydroxymethyl, in the 1,2-position, if desired, functionally modifying a substituent $R^{201}$ in a resulting 1,2-epoxide of the formula

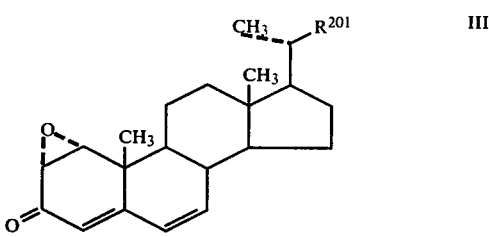

wherein $R^{201}$ is as above and reductively cleaving the resulting compound to the 1,3-diol of formula I and, if desired, esterifying or etherifying the hydroxyl groups, and/or modifying the $R^{201}$ substituent functionally.

Readily cleavable etherified hydroxymethyl groups denoted by $R^{201}$ are preferably groups of the formula —$CH_2Z$ in which Z represents a group of the formula $R^X$—O—$C(R^J, R^Z)$—O—in which $R^J$, $R^X$ and $R^Z$ have the significance given earlier.

The oxidation of a compound of formula II to a 1,2-epoxide of formula III can be suitably accomplished with hydrogen peroxide in the presence of a base, for example, an aqueous-alcoholic alkali hydroxide solution. The reductive cleavage of a compound of formula III to the 1,3-diol can be accomplished with alkali metal in amines, preferably sodium or lithium in ammonia, and, if necessary, followed by treatment with sodium borohydride. The etherification or esterification of the 1- and 3-hydroxy groups can be carried out by known methods, for example, by treatment with dihydropyran in the presence of catalytic amounts of p-toluenesulfonic acid (for the purpose of preparing a tetrahydropyranyl ether) or by treatment with an acid anhydride, such as acetic anhydride, in the presence of a base, such as pyridine (for the purpose of preparing the 3-mono- or 1,3-diacetate).

As functional modification of the substituent $R^{201}$ in a 1,2-epoxide of formula III ether cleavage and etherification should be mentioned. As functional modification of a substituent $R^{201}$ in a 1,3-diol product, ether cleavage, etherification, saponification and esterification, as well as oxidation of the hydroxymethyl group to the formyl or carboxy group and the reduction of a so-obtained formyl, carboxy or carbalkoxy group should be mentioned.

The oxidation of the 20-hydroxymethyl group can be accomplished, for example, by dimethylsulfoxide according to Pfitzner-Moffat, which chromic acid/pyridine, manganese dioxide or pyridinium chlorochromate. The oxidation of the 20-formyl group can be accomplished, for example, with silver oxide. For the reduction of the 20-formyl group, sodium borohydride, for example, can be mentioned. For that of the carboxy group, lithium aluminum hydride, for example, can be mentioned.

The etherification of a 20-hydroxymethyl group can be carried out by means of dihydropyran or alkoxyvinyl ethers, such as 2-methoxypropane. The cleavage of such ethers can be accomplished by treatment with acids as described above for the cleavage of ether groups in the 1- and 3-positions.

The compounds of formula II can be prepared from compounds of the formula

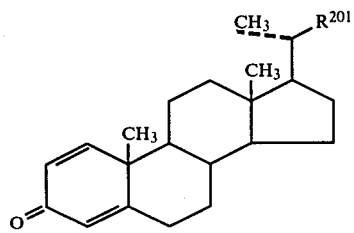

IV wherein $R^{201}$ is as before by treatment of a compound of formula IV with a base, such as potassium tert.-butoxide or sodium hydride in hexamethylphosphoroamide, to convert it into a compound of the formula

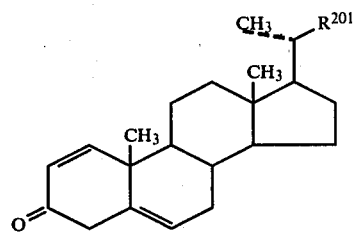

V wherein $R^{201}$ is as before and the compound of formula V can be dehydrogenated by treatment with dehydrogenation agents, such as dichlorodicyanobenzoquinone or chloranil.

(20S)-21-Hydroxy-20-methyl-pregna-1,4,6-trien-3-one of formula II can also be prepared by brominating (20S)-21-hydroxy-20-methyl-pregna-1,4-dien-3-one of formula IV in the 6-position and dehydrobrominating the resulting (20S)-6-bromo-21-hydroxy-20-methyl-pregna-1,4-dien-3-one in the 6,7-position. The bromination can be carried out, for example, using N-bromosuccinimide in the presence of azoisobutyronitrile in a solvent such as carbon tetrachloride, and the dehydrobromiantion can be carried out, for example, using lithium carbonate and lithium bromide in a solvent such as dimethylformamide.

The 21-hydroxy-20-methylpregna-1,4,6-trien-3-one can also be prepared by subjecting 21-hydroxy-20-methyl-6β-methoxy-3α,5-cyclo-5α-pregnane to a retro-i-rearrangement and either oxidizing the obtained 3β,21-dihydroxy-20-methyl-pregna-5-ene directly to 21-hydroxy-20-methylpregna-1,4,6-trien-3-one or first oxidizing it to 21-hydroxy-20-methylpregna-4,6-dien-3-one and then dehydrogenating the latter in the 1,2-position.

21-Hydroxy-20-methyl-pregna-1,4,6-trien-3-one can also be prepared by subjecting 21-acetoxy-6β-methoxy-20-methyl-3α,5-cyclo-5α-pregnane to a retro-i-rearrangement, oxidising the resulting 21-acetoxy-3β-hydroxy-20-methyl-pregn-5-ene to 21-acetoxy-20-methyl-pregna-1,4,6-trien-3-one and saponifying the latter.

The retro-i-rearrangement can be accomplished by treatment with a strong acid, for example, a mineral acid, such as hydrochloric acid, or an organic sulfonic acid, such as p-toluenesulfonic acid. The rearrangement can be carried out in a reaction medium, such as dioxane-water or acetone-water.

The direct conversion of the 3β,21-dihydroxy-20-methylpregna-5-ene or the 21-acetate thereof into the 21-hydroxy-20-methylpregna-1,4,6-trien-3-one or the 21-acetate thereof can be accomplished by treatment with substituted benzoquinones, such as dichlorodicyanobenzoquinone. The oxidation of the 3β,21-dihydroxy-20-methylpregna-5-enes to the 20-hydroxy-20-methylpregna-4,6-dien-3-ones can be performed, for example, with bromine in dimethylformamide in the presence of lithium carbonate and lithium bromide. The 1,2-dihydrogenation of the obtained, 4,6-dienes can be performed with substituted benzoquinones such as 2,3-dichloro-5,6-dicyanobenzoquinone (DDQ). The saponification of 21-acetoxy-20-methyl-pregna-1,4,6-trien-3-one can be carried out, for example, using sodium hydroxide in ethanol.

The compounds of formulas II, III and V and the 21-hydroxy-20-methylpregna-4,6-dien-3-one are new and likewise are the subject of the invention.

The compounds of formula I are intermediates for the preparation of derivatives of cholecalciferols (vitamin D₃), for example, for 1α-hydroxycholecalciferol and 1α,25-dihydroxycholecalciferol. The conversion of a compound of formula I into 1α,25-dihydroxycholecalciferol IX can be accomplished by way of example according to the following synthetic route:

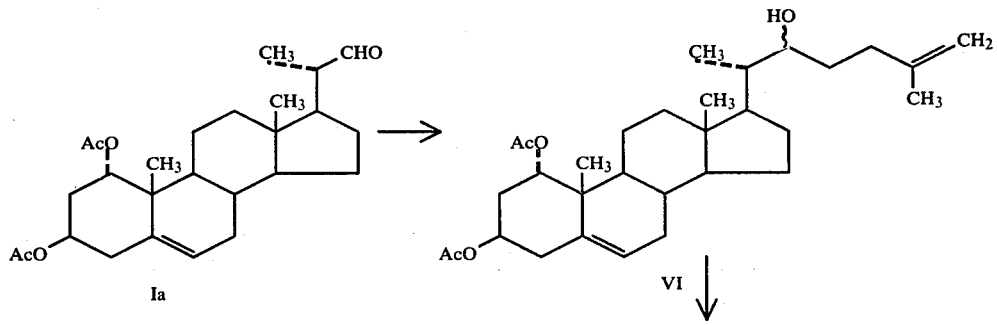

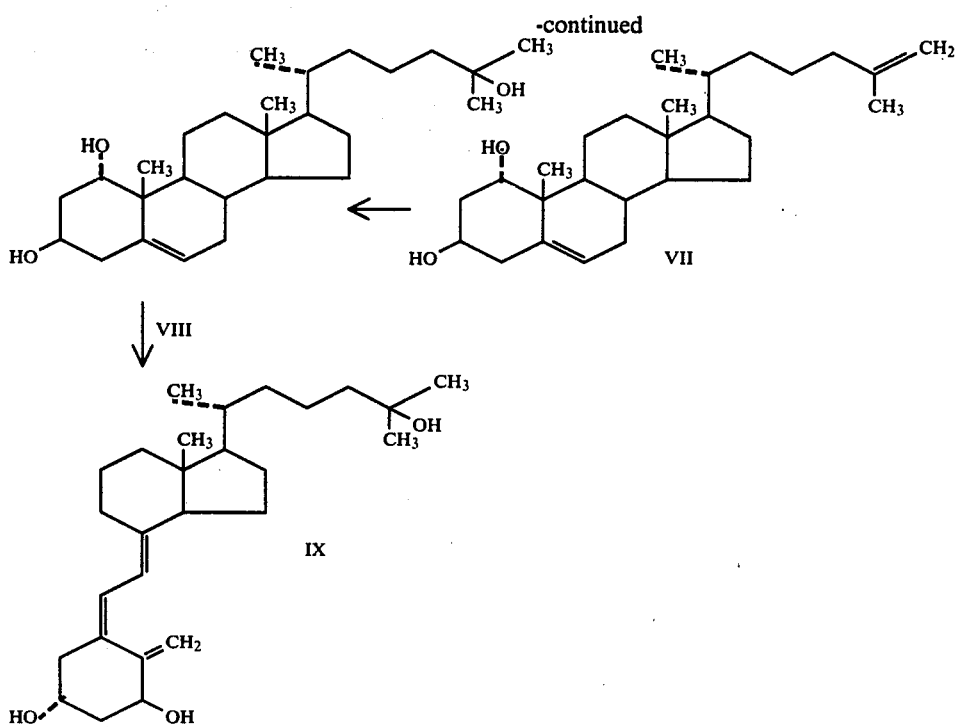

The conversion of a compound of formula Ia, in which AcO stands for an esterified hydroxy group, for example, for acetoxy, can be performed by means of the Grignard reaction with 4-chloro-2-methylbut-1-en in tetrahydrofuran at about −20°. From the compound VI one obtains with methanesulfonylchloride in pyridine the corresponding 22-mesylate, which affords the cholesta-5,25-dien-1α,3β-ol VII by treatment with lithium aluminum hydride in tetrahydrofuran with warming. Treatment of VII with mercuric acetate in tetrahydrofuran-water and then with sodium borohydride-sodium hydroxide yields the cholest-5-en-1α,3β,25-triol VIII, which can be converted into 1α,25-dihydroxyvitamin $D_3$ in known ways.

The following examples illustrate the invention. Temperatures are given in degrees Centigrade.

EXAMPLE 1

A solution of 39.9 g. of (20S)-20-methyl-21-tetrahydropyranyloxypregna-1,4,6-trien-3-one in 1.38 l. of methanol was treated with a solution of 0.92 g. of potassium hydroxide in 9.2 ml. of methanol and 59.2 ml. of 30% hydrogen peroxide. After stirring for 6 hours at 20°, the reaction mixture was poured into 1.4 l. of water and extracted with a total of 9 l. of hexane-ether (1:2). The organic phase was washed with a total of 1.2 l. of 20% sodium bisulfite solution, then with 500 ml. of 30% sodium chloride solution, dried over sodium sulfate and concentrated by water-jet vacuum. The residue, 38 g. of a golden oil, was chromatographed on 1.1 kg. of kieselgel with hexane-ether (1:4), to give 22.4 g. (53.9%) of crystalline (20S)-1α,2α-epoxy-20-methyl-21-tetrahydropyranyloxypregna-4,6-dien-3-one, thin-layer chromatographically pure. The product gave white crystals from hexane, m.p. 113.5°-115°; $[\alpha]_D = +176°$ (c=1.0, chloroform); uv (ethanol)$\lambda_{max}$ 292 nm (ε21370).

The starting material can be prepared as follows:

A solution of 20 g. of (20S)-21-hydroxy-20-methylpregna-1,4-dien-3-one in 200 ml. of dry hexamethylphosphorotriamide was treated with 8.8 g. of 50% sodium hydride dispersion in mineral oil and stirred for 68 hours at room temperature in an argon atmosphere. After dilution with 500 ml. of benzene, excess sodium hydride was filtered off and the filtrate was stirred into 5 l. of ice-water. After addition of 300 g. of sodium chloride, the emulsion was extracted with a total of 7.5 l. of ether and the extracts were dried over sodium sulfate and concentrated under water-jet vacuum. The residue gave by chromatography on 600 g. of kieselgel with hexane-ether (20S)-21-hydroxy-20-methylpregna-1,5-dien-3-one. Recrystallization of the product from ether-ethanol gave the product, m.p. 148°-149°, $[\alpha]_D = +65°$ (c=0.5, chloroform); uv (ethanol)$\lambda_{max}$ 227 nm (ε11760).

A solution of 16.0 g. of (20S)-21-hydroxy-20-methylpregna-1,5-dien-3-one in 350 ml. of dry dioxane was treated with 12.1 g. of dichlorodicyanobenzoquinone and then stirred for 6 hours at 100°. After cooling to 20° the mixture was filtered with reaction, the residue was washed with 80 ml. of dioxane and the combined filtrates were evaporated at 40° under water jet vacuum. The residue was dissolved in 800 ml. of ether-methylene chloride (2:1) and washed successively with 390 ml. of 40% sodium bisulfite solution, 750 ml. of 2 N sodium hydroxide and 400 ml. of 30% sodium chloride solution. The residue (18.1 g.) obtained by drying over sodium sulfate and evaporation under water jet vacuum was chromatographed on 800 g. of aluminum oxide (activity III). Elution with ether-acetic acid (1:1) gave 13.7 g. (85%) of pure (20S)-21-hydroxy-20-methylpregna-1,4,6-trien-3-one. Recrystallization from ether gave light yellow colored crystals of m.p. 156°-157°; $[\alpha]_D = -8.4°$ (c=0.5, chloroform); uv (ethanol): $\lambda_{max}$ 244 nm (ε11700), 256 nm (ε9980) and 302 nm (12220).

A solution of 13.0 g. of (20S)-21-hydroxy-20-methylpregna-1,4,6-trien-3-one in 300 ml. of absolute benzene was added to 9.1 ml. of 3,4-dihydro-2H-pyran and 0.091 g. of water-free p-toluenesulfonic acid and the mixture was allowed to stand for 1 hour at room temperature. The solution was diluted with 500 ml. of ether, washed with 250 ml. of saturated sodium bicarbonate solution, then with a total of 500 ml. of 30% sodium chloride solution and dried over sodium sulfate. The residue (17.6 g.) obtained by filtration and evaporation under water jet vacuum was chromatographed over and 500 g. of kieselgel with ether to give 14.2 g. (86%) of crystalline, thin-layer chromatographically pure (20S)-20-methyl-21-tetrahydropyranyloxypregna-1,4,6-trien-3-one. After recrystallization from hexane, the product melted at 101°–102°; $[\alpha]_D = -5.7°$ (c = 1.0, chloroform); uv (ethanol): $\lambda_{max}$ 223.5 nm ($\epsilon$11200), 254.5 nm ($\epsilon$10090) and 301.5 nm ($\epsilon$11630).

EXAMPLE 2

To a solution of 0.91 g. of lithium in 260 ml. of liquid ammonia was added dropwise over 45 minutes with stirring at −33° a solution of 3.0 g. of (20S)-1α,2α-epoxy-20-methyl-21-tetrahydropyranyloxypregna-4,6-dien-3-one in 170 ml. of absolute ether. After stirring for an additional 15 minutes, isopropanol was added dropwise over about 10 minutes until there was a color change and then a total of 14.3 g. of ammonium chlorite was added portionwise over about 5 minutes. The ammonia was distilled, 30 ml. of ice cold saturated ammonium chloride solution was added slowly to the residue cooled to −25° and the reaction product was taken up in a total of 150 ml. of ice cold ether. The extract was washed with 50 ml. of ice cold 30% sodium chloride solution and evaporated to about 80 ml. at 0° under water jet vacuum. The concentrate was cooled to −15° and added dropwise over 15 minutes to a stirred mixture of 96 ml. of methanol, 9.6 ml. of water and 0.96 g. of sodium borohydride cooled to −70°. The mixture was stirred an additional hour at −70°, then poured into 1 l. of 1% acetic acid at 0° and 73 g. of sodium bicarbonate was added. After dilution with 450 ml. of water, the mixture was extracted with a total of 2 l. of ethyl acetate and the extract was evaporated under water jet vacuum. The residue (3.44 g.) gave by chromatography on 50 g. of kieselgel with hexane-ether mixtures, increasing containing ether from 0 to 50%, in the hexane-ether (1:1) eluant, 1.833 g. of crude (20S)-1α,3β-dihydroxy-20-methyl-21-tetrahydropyranyloxypregna-5-ene. A solution of the crude diol in 27 mol of pyridine was treated with 27 ml. of acetic anhydride and 0.025 g. of 4-dimethylaminopyridine and stored at room temperature for 48 hours. The solution was poured onto a mixture of 200 ml. of saturated sodium bicarbonate solution and extracted with a total of 300 ml. of ether. The extract was washed with water, dried over sodium sulfate and evaporated at 40° under water pump vacuum. Chromatography of the residue (2.83 g.) on 84 g. of kieselgel with hexane-ether (9:1) gave 1.69 g. (46.5%) of pure crystalline (20S)-1α,3β-diacetoxy-20-methyl-21-tetrahydropyranyloxypregna-5-ene. The product, after recrystallization from hexane, melted at 138°–138.5°; $[\alpha]_D = -7°$ (c = 1.0, chloroform).

EXAMPLE 3

A solution of 1.3 g. of (20S)-1α,3β-diacetoxy-20-methyl-21-tetrahydropyranyloxypregna-5-ene in 13 ml. of acetic acid was treated with 4 ml. of water and warmed to 80°. After the addition of 6 ml. of water, the mixture was left at 80° for one hour, cooled and poured into 100 ml. of water. The product was extracted with 100 ml. of ether, the extract was washed with saturated sodium bicarbonate, then with 30% sodium chloride solution and dried over sodium sulfate. After filtration and evaporation under water jet vacuum, 1.19 g. of residue was obtained. This was chromatographed on 25 g. of kieselgel with hexane-ether (4:1) to give 0.938 g. (80%) of pure crystalline (20S)-1α,3β-diacetoxy-21-hydroxy-20-methylpregna-5-ene. Recrystallization from ether-hexane gave white needles of m.p. 134.5°–135°; $[\alpha]_D = -28°$ (c = 0.5, chloroform).

EXAMPLE 4

To a solution of 1.5 g. of (20S)-1α,3β-diacetoxy-20-methyl-21-tetrahydropyranyloxypregna-5-ene in 25 ml. of absolute ether was added 0.3 g. of lithium aluminum hydride and the suspension was stirred at room temperature for 1 hour. After cooling to 0°, 2 ml. of ethyl acetate was added and the mixture poured onto ice-water. The insoluble part was extracted with ethyl acetate, the organic solution was washed with water and dried over sodium sulfate. By filtration and evaporation under vacuum 1.4 g. of crystalline (20S)-1α,3β-dihydroxy-20-methyl-21-tetrahydropyranyloxypregna-5-ene was obtained. Recrystallization from methanol gave white crystals, m.p. 138°–141°; $[\alpha]_D = -48.8°$ (c = 0.5, chloroform).

EXAMPLE 5

A solution of 0.69 g. of (20S)-1α,3β-dihydroxy-20-methyl-21-tetrahydropyranyloxypregna-5-ene in 6.9 ml. of acetic acid and 2.1 ml. of water was warmed to 80° and an additional 3.2 ml. of water was added. The mixture was kept at 80° for one hour, cooled and poured into water. The suspension was extracted with ethyl acetate and the organic solution was washed with saturated sodium bicarbonate solution and water. After drying and evaporation under vacuum, 0.6 g. of (20S)-20-methyl-1α,3β,21-trihydroxypregna-5-ene was obtained. Recrystallization from acetone gave 0.3 g. of colorless prisms, m.p. 208°–209°; $[\alpha]_D = -29°$ (c = 0.5, methanol).

EXAMPLE 6

A solution of (20S)-1α,3β-diacetoxy-21-hydroxy-20-methylpregna-5-ene in 5 ml. of dimethylsulfoxide and 5 ml. of benzene was treated with 0.24 ml. of pyridine, 0.12 ml. of trifluoroacetic acid and 1.85 g. of dicyclohexylcarbodiimide. The mixture was kept at room temperature for 23 hours and then a solution of 0.5 g. of water free oxalic acid in 5 ml. of ether was added dropwise. After 45 minutes of stirring at room temperature, the suspension was filtered under suction and the residue was worked with ether. The filtrate was worked with saturated sodium bicarbonate solution, with water until neutral and dried over sodium sulfate. The residue obtained by evaporation was chromatographed on 25 g. of kieselgel with hexane-ether (4:1) to give 0.713 g. of amorphous (20S)-1α,3β-diacetoxy-20-methylpregna-5-en-21-ol; $[\alpha]_D = -37°$ (c = 0.5, chloroform).

EXAMPLE 7

A solution of 127.4 mg. of silver nitrate in 6 ml. of absolute ethanol was treated with 215.3 mg. of (20S)-1α,3β-diacetoxy-20-methylpregna-5-en-21-ol, and with stirring a solution of 4 ml. of ethanol and 0.36 ml. of 5 N sodium hydroxide was added dropwise. The mixture was stirred at room temperature for 24 hours, filtered under vacuum and the filtrate, after addition of 20 ml. of 1 N sodium hydroxide was allowed to stand at room temperature overnight. The solution was freed of alcohol under vacuum and acidified by the addition of dilute sulfuric acid. The precipitated crude acid gave, after suction filtration and recrystallization from methanol-water (3:2), 103 mg. of (20S)-1α,3β-dihydroxy-20-methylpregna-5-en-21-carboxylic acid in the form of white needles, m.p. 268°–270°; $[α]_D = -41°$ (c=0.5, methanol).

EXAMPLE 8

A solution of 4.31 g. of (20S)-21-hydroxy-20-methyl-6β-methoxy-3α,5-cyclo-5α-pregnane in 200 ml. of dioxane-water (3:1) was treated with 0.25 g. of p-toluenesulfonic acid hydrate and stirred at 80° for 1 hour. After cooling, 3 ml. of 10% sodium carbonate solution was added and the mixture was evaporated at 40° under water-jet vacuum. The crystalline residue was treated with water. The suspension was filtered under suction and the residue was washed with water and dried to give 4.1 g. of (20S)-3β,21-dihydroxy-20-methylpregna-5-ene, m.p. 194°–202°. Recrystallization from ethyl acetate gave 3.4 g. of colorless needles, m.p. 196°–204°; $[α]_D = -60°$ (c=0.5, chloroform).

EXAMPLE 9

To a boiling solution of 3.0 g. of (20S)-3β,21-dihydroxy-20-methylpregna-5-ene in 36 ml. of dry dioxane was added a solution of 7.16 g. of dicyanodichlorobenzoquinone in 38 ml. of dry dioxane dropwise over 2 hours at 100° and the reaction mixture was stirred at 100° for 3 hours. After cooling to 20° the suspension was filtered with suction, the filter cake was washed with 40 ml. of dioxane and the filtrate was evaporated at 45° under water-jet vacuum. The residue was taken up in 200 ml. of methylene chloride, the solution was washed with 50 ml. of 40% sodium bisulfite solution, then with 80 ml. of 2 N sodium hydroxide, finally with water, dried over sodium sulfate and, after filtration, evaporated under water-jet vacuum. The residue (2.1 g.) was chromatographed on 70 g. of neutral aluminum oxide (activity II). Elution first with hexane-ether (1:1), then with ether gave in the ether eluant 0.9 g. (30.6%) of (20S)-21-hydroxy-20-methylpregna-1,4,6-trien-3-one. Recrystallization from ether gave light yellow colored flakes, m.p. 156°–157°; $[α]_D = -8.4°$ (c=0.5, chloroform); uv (ethanol): $λ_{max}$ 224 nm (ε=11700), 256 nm (ε=99807) and 302 nm (ε=12220).

EXAMPLE 10

To a suspension prepared from 1.66 g. of (20S)-3β,21-dihydroxy-20-methylpregnan-5-ene, 35 ml. of dimethylformamide, 2.25 g. of lithium carbonate and 1.08 g. of lithium bromide, a solution of 1.75 g. of bromine in 5 ml. of dimethylformamide was added dropwise at 75° over 20 minutes. The suspension was stirred at this temperature for 45 minutes, cooled and added to 300 ml. of ice water. The emulsion was extracted with ether, the ethereal solution was washed with water and dried over sodium sulfate. The residue (1.7 g.) obtained by filtration and evaporation was chromatographed on 85 g. of kieselgel with methylene chloride-acetone (95:1) to yield 1.12 g. of thin-layer chromatographically pure crystalline (20S)-21-hydroxy-20-methylpregna-4,6-diene-3-one. Recrystallization from ether gave pale yellow flakes, m.p. 144°–145°; $[α]_D = +37.5°$ (c=1, chloroform); uv (ethanol): $λ_{max}$ 284 nm (ε=26760).

EXAMPLE 11

A solution of 1.7 g. of (20S)-21-hydroxy-20-methylpregna-4,6-dien-3-one in 80 ml. of dry benzene was treated with 1.45 g. of dichlorodicyano and then heated under reflux for 10 hours. The resulting suspension was filtered under suction, the filtrate was washed with 5% sodium hydroxide, then with water and dried over sodium sulfate. The residue obtained by evaporation was taken up in methylene chloride and filtered through a column of 10 g. of aluminum oxide. From the filtrate, 1 g. of crude crystals were obtained, were recrystallized from ether to give (20S)-21-hydroxy-20-methylpregna-1,4,6-trien-3-one, m.p. 156°–157°. This was shown to be identical to the compound obtained in Example 8 according to its thin layer chromatogram mixture, melting point and infrared spectrum.

EXAMPLE 12

A solution of 2.0 g of (20S)-21-acetoxy-6β-methoxy-20-methyl-3α,5-cyclo-5α-pregnane in 62 ml. of dioxan and 21 ml. of water was treated with 0.1 g of p-toluenesulphonic acid and held at 80° C. for 1 hour. The solution was cooled to 20° C., treated with 3 ml. of saturated sodium carbonate solution and concentrated in vacuo. The residue was taken up in methylene chloride and water, the organic phase was washed with saturated sodium chloride solution and dried over sodium sulphate. The residue obtained after filtration and concentration was subjected to chromatography on 100 g of silica gel using methylene chloride/acetone (99:1) for the elution, there being obtained 1.78 g of (20S)-21-acetoxy-3β-hydroxy-20-methyl-pregn-5-ene. The product crystallised from ether/hexane in the form of white flakes of melting point 143° C.; $[α]_D = -43.8°$ (c=0.9 in chloroform).

To a boiling solution of 1.54 g of (20S)-21-acetoxy-3β-hydroxy-20-methyl-pregn-5-ene in 16 ml. of dry dioxan was added dropwise at 100° C. within 1 hour a solution of 3.73 g of dichlorodicyanobenzoquinone in 20 ml. of dry dioxan and the mixture was stirred at 100° C. for 3.5 hours. After cooling to 20° C., the suspension was filtered, the residue was washed with 30 ml. of dioxan and the filtrate was concentrated at 40° C. in vacuo. The residue was taken up in methylene chloride and washed successively with 20% sodium bicarbonate solution, 1-N sodium hydroxide and water and then dried over sodium sulphate. The residue (2.2 g of resin) obtained after filtration and concentration was subjected to chromatography on 100 g of silica gel using methylene chloride/acetone (49:1) for the elution, there being obtained 0.87 g (58%) of (20S)-21-acetoxy-20-methyl-pregna-1,4,6-trien-3-one of melting point 90°–93° C.; $[α]_D = -18.8°$ (c=1.0 in chloroform); UV (ethanol): $λ_{max}$ 233 nm (ε=11115), 253 nm (ε=9900) and 300 nm (ε=11150).

A solution of 0.8 g of (20S)-21-acetoxy-20-methyl-pregna-1,4,6-trien-3-one in 12 ml. of ethanol was treated with 6.5 ml. of 1-N sodium hydroxide and left at room temperature overnight. The solution was neutralised with glacial acetic acid and concentrated in vacuo. The residue was taken up in methylene chloride, washed with water and dried over sodium sulphate. The crystalline residue obtained after filtration and concentration gave, after recrystallisation from ether, (20S)-21-hydroxy-20-methyl-pregna-1,4,6-trien-3-one in the form of yellowish crystals of melting point 156°–157° C.

EXAMPLE 13

To a boiling solution of 5.2 g of (20S)-21-hydroxy-20-methyl-pregna-1,4-dien-3-one in 300 ml. of carbon tetrachloride were added 3.4 g of N-bromosuccinimide and 0.16 g of azoisobutyronitrile and the mixture was boiled under reflux for 30 minutes. The suspension obtained was cooled to 50° C., filtered and the residue was washed with carbon tetrachloride. The combined filtrates were concentrated in vacuo to give, as the residue, an oily C(6) epimer mixture of (20S)-6-bromo-21-hydroxy-20-methyl-pregna-1,4-dien-3-one. This was dissolved in 50 ml. of dimethylformamide, treated with 1.3 g of lithium carbonate and 1.4 g of lithium bromide and the mixture was boiled under reflux for 4 hours under an argon atmosphere. The cooled mixture was added dropwise to 400 ml. of ice-water and the separated crude (20S)-21-hydroxy-20-methyl-pregna-1,4,6-trien-3-one was filtered off under suction.

The dried crude product obtained according to the preceding paragraph was dissolved in 100 ml. of methanol, 1.4 ml. of 10% methanolic sodium hydroxide were added and 6 ml. of 30% hydrogen peroxide were added dropwise at 5°–7° C. while stirring within 10 minutes. After stirring at 7° C. for 45 minutes and at 20° C. for 2 hours, the mixture was added to 1.1 liters of 5% sodium chloride solution and extracted with ether. The extract was washed with 20% sodium bicarbonate solution and water, dried over sodium sulphate and concentrated in a water-jet vacuum. The residue was chromatographed on 100 g of silica gel using hexane/ether (4:1) for the elution and recrystallised from methanol/ether to give 1.4 g of pure (20S)-1α,2α-epoxy-21-hydroxy-20-methyl-pregna-4,6-dien-3-one of melting point 158°–161° C.; $[\alpha]_D = +213.0°$ (c=0.25 in chloroform); UV (ethanol): $\lambda_{max}$ 292 nm ($\epsilon = 19380$).

EXAMPLE 14

1.8 ml. of 3,4-dihydro-2H-pyran and 20 mg of anhydrous p-toluenesulphonic acid were added to a solution of 2.45 g of (20S)-1α,2α-epoxy-21-hydroxy-20-methyl-pregna-4,6-dien-3-one in 125 ml. of absolute benzene. After standing at room temperature for 1 hour, the solution was diluted with ether, washed with saturated sodium bicarbonate solution and water, dried over sodium sulphate and concentrated in a water-jet vacuum. The residue was chromatographed on 30 g of silica gel using hexane/ether (4:1) for the elution, there being obtained 2.0 g (65%) of (20S)-1α,2α-epoxy-20-methyl-21-tetrahydropyranyloxy-pregna-4,6-dien-3-one. After recrystallisation from hexane, the product melted at 101°–102° C. and was shown by thin-layer chromatography, mixed melting point and IR spectrum to be identical with the compound prepared as described in Example 7.

EXAMPLE 15

A solution of 1.0 g of (20S)-1α,3β-dihydroxy-20-methyl-pregn-5-ene-21-carboxylic acid in 50 ml. of methanol was treated with an ethereal solution containing 4 mmol of diazomethane and stored at room temperature for 30 minutes. After addition of glacial acetic acid, the mixture was concentrated in vacuo. The crystalline residue, which was uniform according to thin-layer chromatography, was recrystallised from concentrated methanolic solution to give 0.79 g of (20S)-1α,3β-dihydroxy-20-methyl-pregn-5-ene-21-carboxylic acid methyl ester in the form of colourless prisms of melting point 144°–146° C.; $[\alpha]_D = -56°$ (c=0.5 in chloroform). Each mol of this ester contained 1 mol of methanol of crystallisation.

EXAMPLE 16

A solution of 0.101 g of (20S)-1α,3β-dihydroxy-20-methyl-pregn-5-ene-21-carboxylic acid methyl ester in 2 ml. of pyridine was treated with 2 ml. of acetic anhydride and then with 5 mg of 4-dimethylaminopyridine and left at room temperature for 48 hours. The mixture was poured on to ice-water and the product was extracted with ether. The ethereal solution was washed with 2-N hydrochloric acid, saturated sodium bicarbonate solution and water, dried over sodium sulphate and concentrated in vacuo. The residue (0.113 g) was recrystallised from ether/methanol and gave (20S)-1α,3β-diacetoxy-20-methyl-pregn-5-ene-21-carboxylic acid methyl ester in the form of colourless prisms of melting point 123°–124° C.; $[\alpha]_D = -34°$ (c=0.25 in chloroform).

EXAMPLE 17

A solution of 0.875 g of (20S)-1α,3β-dihydroxy-20-methyl-pregn-5-ene-21-carboxylic acid methyl ester in 40 ml. of absolute benzene was treated with 10 mg of anhydrous p-toluene-sulphonic acid and 1.5 ml. of 3,4-dihydro-2H-pyran and stored at room temperature for 24 hours. The solution was diluted with ether, washed with saturated sodium bicarbonate solution and dried over sodium sulphate. After concentration and drying in vacuo, there were obtained 1.2 g of oily (20S)-1α,3β-di(tetrahydropyranyloxy)-20-methyl-pregn-5-ene-21-carboxylic acid methyl ester; $[\alpha]_D = -12°$ (c=0.5 in chloroform).

EXAMPLE 18

A solution of 1.09 g of (20S)-1α,3β-di(tetrahydropyranyloxy)-20-methyl-pregn-5-ene-21-carboxylic acid methyl ester in 7 ml. of absolute tetrahydrofuran was added dropwise at room temperature within 10 minutes while stirring to a suspension of 0.25 g of lithium aluminium hydride in 10 ml. of absolute tetrahydrofuran. After stirring at room temperature for 1 hour, there were successively added dropwise 2 ml. of ethyl acetate, 10 ml. of tetrahydrofuran/water (9:1) and 30 ml. of 0.5-N sodium hydroxide. The mixture was freed from the organic solvents in vacuo and the aqueous residue was extracted with ether. The ethereal extract was washed with water, dried over sodium sulphate, concentrated and the residue was dried in vacuo, there being obtained 1.02 g of (20S)-1α,3β-di(tetrahydropyranyloxy)-21-hydroxy-pregn-5-ene in the form of a foam which melted at 50°–67° C. but which could not be recrystallised; $[\alpha]_D = -5.3°$ (c=1.0 in chloroform).

EXAMPLE 19

A solution of 55.1 mg of p-toluenesulphonyl chloride in 0.2 ml. of dry pyridine was added at 0° C. to a solution of 100 mg of (20S)-1α,3β-diacetoxy-21-hydroxy-20-methyl-pregn-5-ene in 0.5 ml. of dry pyridine. After standing at 0° C. for 6 hours, the mixture was poured on to ice-water and extracted with ether. The extract was washed successively with 2-N hydrochloric acid, water, saturated sodium bicarbonate solution and water. The residue obtained after drying over sodium sulphate and concentration was chromatographed on 3.5 g of silica gel using hexane/ether (4:1) for the elution, there being obtained 100 mg of uniform (20S)-1α,3β-diacetoxy-20-methyl-21-(p-toluene-sulphonyloxy)-pregn-5-ene. After recrystallisation from ether, the product melted at 168°–170° C.; $[\alpha]_D = -20.8°$ (c=0.5 in chloroform).

EXAMPLE 20

A solution of 0.54 g of (20S)-1α,3β-diacetoxy-21-hydroxy-20-methyl-pregn-5-ene and 0.825 g of carbon tetrabromide in 10 ml. of ether was treated with 0.625 g of triphenylphosphine and the mixture was left at room temperature for 16 hours. After dilution with ether, insoluble material was filtered off. The filtrate was concentrated in vacuo and the residue was chromatographed on 15 g of silica gel using hexane/ether (9:1) for the elution. There was obtained 0.55 g of uniform (20S)-21-bromo-1α,3β-diacetoxy-20-methyl-pregn-5-ene in the form of a colourless powder of melting point 75°–76° C.; $[\alpha]_D = -13.8°$ (c=0.5 in chloroform).

We claim:

1. A compound of the formula

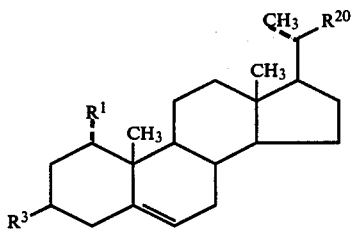

wherein $R^1$ and $R^3$ are hydroxy, formyloxy, alkanoyloxy having 2 to 4 carbon atoms or a group of the formula $$R^XOC(R^J, R^Z)\text{---}O\text{---}$$

wherein $R^J$ is hydrogen or alkyl having 1 to 6 carbon atoms; $R^X$ and $R^Z$ are alkyl having 1 to 6 carbon atoms or taken together $R^X$ and $R^Z$ are alkylene of 3 to 6 carbon atoms; and $R^{20}$ is hydroxymethyl, formyloxymethyl, alkanoyloxymethyl having 2 to 4 carbon atoms in the alkanoyloxy moiety, bromomethyl, 4-toluenesulfonyloxymethyl, carboxyl or carbalkoxy.

2. The compound of claim 1 which is (20S)-1α,3β-dihydroxy-20-methyl-21-tetrahydropyranyloxypregna-5-ene.

3. The compound of claim 1 which is (20S)-1α,3β-diacetoxy-20-methyl-21-tetrahydropyranyloxypregna-5-ene.

4. The compound of claim 1 which is (20S)-1α,3β-diacetoxy-21-hydroxy-20-methyl-pregna-5-ene.

5. The compound of claim 1 which is (20S)-1α,3β-dihydroxy-20-methyl-21-tetrahydropyranyloxypregna-5-ene.

6. The compound of claim 1 which is (20S)-20-methyl-1α,3β,21-trihydroxy-pregna-5-ene.

7. The compound of claim 1 which is (20S)-1α,3β-diacetoxy-20-methylpregna-5-en-21-al.

8. The compound of claim 1 which is (20S)-1α,3β-dihydroxy-20-methylpregna-5-en-21-carboxylic acid.

9. A compound of the formula

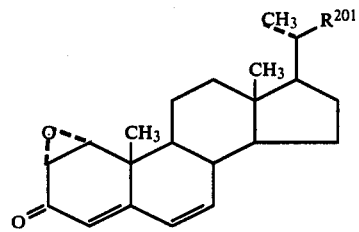

wherein $R^{201}$ is hydroxymethyl or a group of the formula $$R^XOC(R^J, R^Z)\text{---}O\text{---}CH_2\text{---}$$

wherein $R^J$ is hydrogen or alkyl having 1 to 6 carbon atoms; $R^X$ and $R^Z$ are alkyl having 1 to 6 carbon atoms or taken together $R^X$ and $R^Z$ are alkylene of 3 to 6 carbon atoms.

10. The compound of claim 9 which is (20S)-1α,2α-epoxy-20-methyl-21-tetrahydropyranyloxypregna-4,6-dien-3-one.

11. A compound of the formula

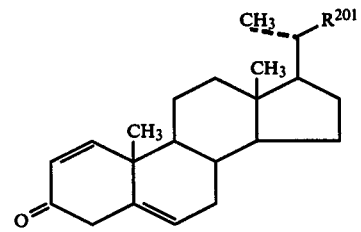

wherein $R^{201}$ is hydroxymethyl or a group of the formula $$R^XOC(R^J, R^Z)\text{---}O\text{---}CH_2\text{---}$$

wherein $R^J$ is hydrogen or alkyl having 1 to 6 carbon atoms; $R^X$ and $R^Z$ are alkyl having 1 to 6 carbon atoms or taken together $R^X$ and $R^Z$ are alkylene of 3 to 6 carbon atoms.

12. The compound of claim 11 which is (20S)-21-hydroxy-20-methylpregna-1,5-dien-3-one.

* * * * *

UNITED STATES PATENT AND TRADEMARK OFFICE
CERTIFICATE OF CORRECTION

PATENT NO. : 4,193,921
DATED : March 18, 1980
INVENTOR(S) : Andor Furst, Ludwig Labler and Werner Meier It is certified that error appears in the above—identified patent and that said Letters Patent is hereby corrected as shown below:

Column 13, Line 39 - After "hydroxymethyl," the word "formyl," should be inserted Signed and Sealed this Twenty-eighth Day of October 1980

[SEAL]

Attest:

SIDNEY A. DIAMOND

Attesting Officer

Commissioner of Patents and Trademarks